United States Patent [19]
Fischell et al.

[11] Patent Number: 5,634,928
[45] Date of Patent: Jun. 3, 1997

[54] INTEGRATED DUAL-FUNCTION CATHETER SYSTEM AND METHOD FOR BALLOON ANGIOPLASTY AND STENT DELIVERY

[76] Inventors: Robert E. Fischell, 14600 Viburnum Dr., Dayton, Md. 21036; David R. Fischell, 71 Riverlawn Dr., Fair Haven, N.J. 07704; Tim A. Fischell, 1018 Chancery La., Nashville, Tenn. 37215

[21] Appl. No.: 647,294

[22] Filed: May 9, 1996

Related U.S. Application Data

[63] Continuation of Ser. No. 351,498, Dec. 7, 1994, abandoned.
[51] Int. Cl.$^6$ ............................................. A61M 25/10
[52] U.S. Cl. ............................................ 606/108; 606/194
[58] Field of Search ................................. 606/108, 194

[56] References Cited

U.S. PATENT DOCUMENTS

| | | | |
|---|---|---|---|
| 4,649,922 | 3/1987 | Wiktor | 623/1 X |
| 4,665,918 | 5/1987 | Garza et al. | 606/108 |
| 4,681,110 | 7/1987 | Wiktor | 606/194 |
| 4,732,152 | 3/1988 | Wallsten et al. | 606/108 |
| 4,733,665 | 3/1988 | Palmaz | 606/108 |
| 4,768,507 | 9/1988 | Fischell et al. | 606/108 |
| 4,969,890 | 11/1990 | Sugita et al. | 606/192 |
| 5,019,090 | 5/1991 | Pinchok | 606/194 |
| 5,192,297 | 3/1993 | Hull | 606/108 X |
| 5,222,969 | 6/1993 | Gillis | 606/194 |
| 5,275,622 | 1/1994 | Lazarus et al. | 606/194 X |
| 5,290,295 | 3/1994 | Querals et al. | 606/108 |
| 5,453,090 | 9/1995 | Martinez et al. | 606/108 X |
| 5,458,605 | 10/1995 | Klemm | 606/108 |

FOREIGN PATENT DOCUMENTS

| | | |
|---|---|---|
| 150281 | 8/1985 | European Pat. Off. . |
| 318918 | 6/1989 | European Pat. Off. . |
| 362444 | 4/1990 | European Pat. Off. . |
| 533511 | 3/1993 | European Pat. Off. ............... 606/194 |
| 89/8433 | 9/1989 | WIPO . |

*Primary Examiner*—Michael H. Thaler
*Attorney, Agent, or Firm*—Morton J. Rosenberg; David I. Klein

[57] ABSTRACT

An integrated catheter system utilizes a balloon angioplasty catheter placed through a central passageway of a stent delivery catheter to enable balloon angioplasty and stent delivery to be accomplished with a single device. The integrated catheter system is able to perform dilatation of an arterial stenosis, placement of the stent at the site of the stenosis and then the angioplasty catheter balloon can be used to further embed the stent into the arterial wall. Balloon angioplasty, stent placement and stent embedding into the arterial wall are all accomplished while the catheter's angioplasty balloon remains situated at the site of the stenosis. A conically shaped distal portion of the stent delivery catheter allows stent placement over the deflated balloon after balloon angioplasty even when intimal dissection causes an intimal flap to be pushed inwardly against the deflated balloon. A proximal portion of the integrated catheter system employs longitudinal motion constraining spacers to prevent the stent from being inadvertently positioned beyond the distal end of the balloon. The balloon of the balloon angioplasty catheter can be readily advanced through tortuous coronary arteries because the distal end of the stent delivery catheter can be placed back by 0.5 to 20 cm from the balloons proximal end during insertion. Thus, the stiffness of the stent and the stent delivery catheter do not add stiffness to the distal portion of the balloon angioplasty catheter, which stiffness can prevent catheter advancement through such tortuous vessels.

19 Claims, 10 Drawing Sheets

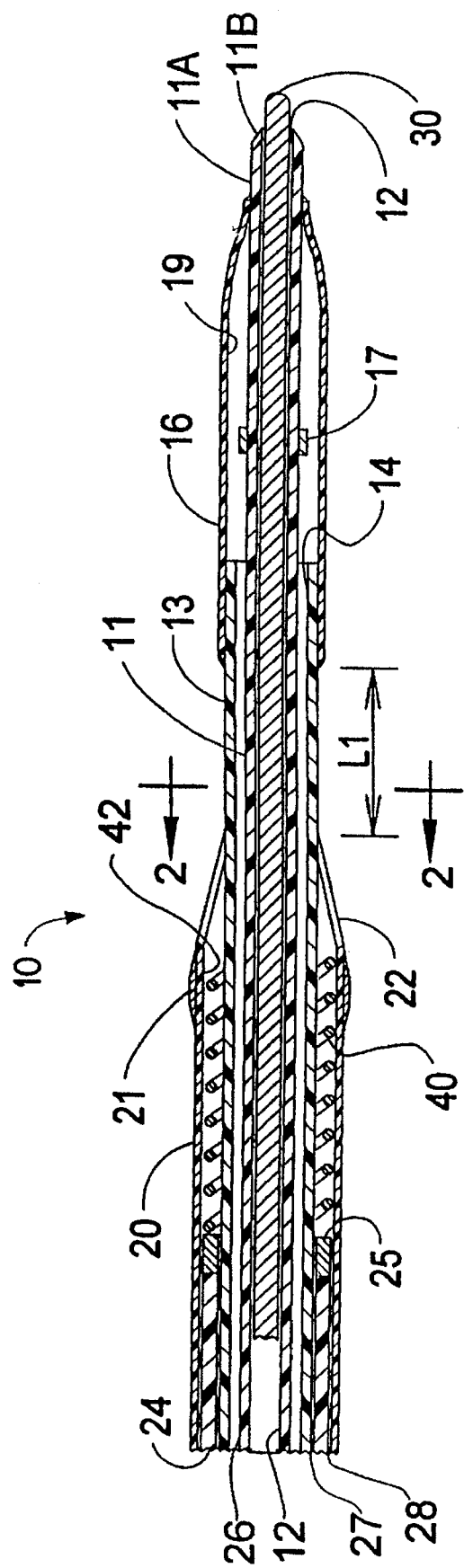
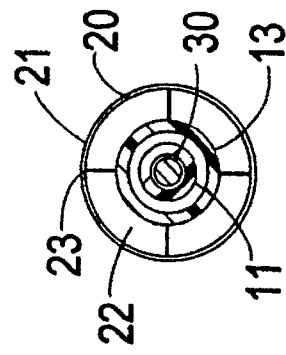
FIG. 1
FIG. 2

INTEGRATED DUAL-FUNCTION CATHETER SYSTEM AND METHOD FOR BALLOON ANGIOPLASTY AND STENT DELIVERY

This application is a continuation of application Ser. No. 08/351,498 filed Dec. 7, 1994, now abandoned.

FIELD OF USE

This invention is generally in the field of devices for opening and maintaining patency within vessels of the human body with specific application to percutaneous transluminal coronary angioplasty (PTCA) and stent delivery into a dilated arterial stenosis.

BACKGROUND OF THE INVENTION

It is well known to use balloon angioplasty catheters for the dilatation of various vessels of the human body and most particularly for opening stenotic arteries. It is also well known to place stents into vessels to maintain patency of that vessel. It is also well known to use a balloon catheter for imbedding a stent into the wall of the vessel to prevent stent migration.

It is typical to use separate catheters for vessel dilatation and for stent delivery. This requires one or more catheter exchanges which increase the time and cost for performing interventional procedures. Since the patient is typically in some discomfort during such procedures, it is also highly advantageous to the patient to make the interventional procedure as short as possible. Furthermore, removing a balloon angioplasty catheter after balloon dilation can result in an intimal dissection that can preclude stent placement.

In U.S. Pat. No. 5,019,090, L. Pinchuk illustrates in FIGS. 13 to 18 a method for mounting a self-deploying stent on a balloon angioplasty catheter. However, Pinchuk's method functions only for self-deploying stents and not balloon expandable stents, and furthermore, his method requires the balloon to be advanced at least 3 cm beyond the distal end of the stenosis that is treated. That is not possible in many coronary arteries because of restrictions within the lumens of the coronary arteries. Furthermore, Pinchuk's method requires two additional steps, i.e. one is a further advancement of the balloon after balloon angioplasty is performed, and later pulling the balloon back within the deployed stent. Pulling back of the balloon catheter can cause the stent to be moved away from its optimal location. Additional steps in such a procedure require additional time which is generally undesirable. Furthermore, Pinchuk does not teach a means or method for the use of a guide wire through the center of the integrated catheter so as to guide it through the typically tortuous coronary vasculature. Still further, Pinchuk teaches an outer sheath with a blunt end whose operability can be defeated because of intimal dissection which often occurs as a result of balloon angioplasty. Still further, Pinchuk does not describe any structure at the catheter's proximal end for the introduction of fluids and a guide wire and for disallowing inadvertent release of the stent.

SUMMARY OF THE INVENTION

The present invention overcomes the disadvantages of prior art devices by integrating a balloon catheter and a stent delivery catheter into a single device which can perform both balloon angioplasty and stent delivery. Although this invention could be used for any vessel of the human body including but not limited to arteries, veins, vascular grafts, billiary ducts, urethras, fallopian tubes, bronchial tubes, etc., the descriptions herein will highlight the use of this device for arterial balloon angioplasty (and specifically PTCA) followed by intra-arterial stenting.

Thus an object of this invention is to perform vessel dilatation, stent placement, and balloon enhanced embedding of the stent into the vessel wall all with a single integrated catheter.

Another object of this invention is to allow the balloon to remain in one place in the artery during (1) balloon angioplasty, (2) stent placement, and finally (3) the further imbedding of the stent into the arterial wall.

Still another object of this invention is to deploy a self-expanding stent by means of pulling back a slideable outer sheath which allows the stent to expand radially outward.

Still another object of this invention is to provide an improved apparatus and method for deploying balloon expandable stents.

Still another object of this invention is to have the integrated catheter capable of being advanced over a flexible guide wire.

Still another object of this invention is to provide a conically shaped distal portion of the outer sheath which can accomplish proper placement of the stent even in cases of severe intimal dissection which could cause an intimal flap that could block the passage of an outer sheath having a blunt end.

Still another object of this invention is to initially place the stent at least several centimeters proximal to the proximal end of the angioplasty balloon thus allowing better trackability of the catheter's distal end over a flexible guide wire and through tortuous coronary arteries and through a long tight stenosis.

Still another object of this invention is to have a means to limit the forward displacement of the integrated catheter's pusher tube to prevent the stent from being pushed beyond the distal end of the balloon.

Still another object of this invention is to provide a separate outer sheath, stent and pusher tube assembly that can be placed over a guide wire or over any balloon angioplasty catheter in the catherization laboratory prior to placement of the entire assembly into a vessel of human body.

Still another object of this invention is to have a removable means to maintain a set spacing between the pusher tube and the outer sheath to preclude the inadvertent and premature release of the stent.

Still another object of this invention is to allow introduction or exchange of balloon angioplasty catheters through a stent delivery catheter already placed in the body or just before placement in the body.

These and other objects and advantages of this invention will become apparent to a person of ordinary skill in this art upon careful reading of the detailed description of this invention including the drawings and claims as presented herein.

BRIEF DESCRIPTION OF THE DRAWINGS

FIG. 1 is a longitudinal cross section of a distal portion of the integrated, dual-function catheter system.

FIG. 2 is a transverse cross section of the catheter at section 2—2 of FIG. 1.

FIG. 4G$_1$ shows the outer sheath pulled back thus releasing the self-expanding stent so that it deploys outward against the vessel wall.

FIG. 4G$_2$ shows a balloon expandable stent as it is placed onto the deflated balloon.

DETAILED DESCRIPTION OF THE INVENTION

Two prior U.S. patent applications (Ser. Nos. 08/273,459 now abandoned and 08/298,214) by the same inventors (which are included herein by reference) describe various means for delivering self-expanding, shape memory metal stents into a vessel of the human body. The invention described herein expands the concepts taught in those prior applications by teaching a dual-function integrated catheter system that has an expandable balloon located near the catheter's distal end whose purposes are to initially dilate a vessel and then, after a stent is deployed, to further imbed that stent into the wall of the vessel. The balloon can also be used to deploy a stent if the stent is not self-expandable. The present design is capable of performing these functions while retaining the balloon at one single longitudinal position within the artery, i.e., at no time is there a need to advance the balloon beyond the stenotic lesion.

Figure 3:
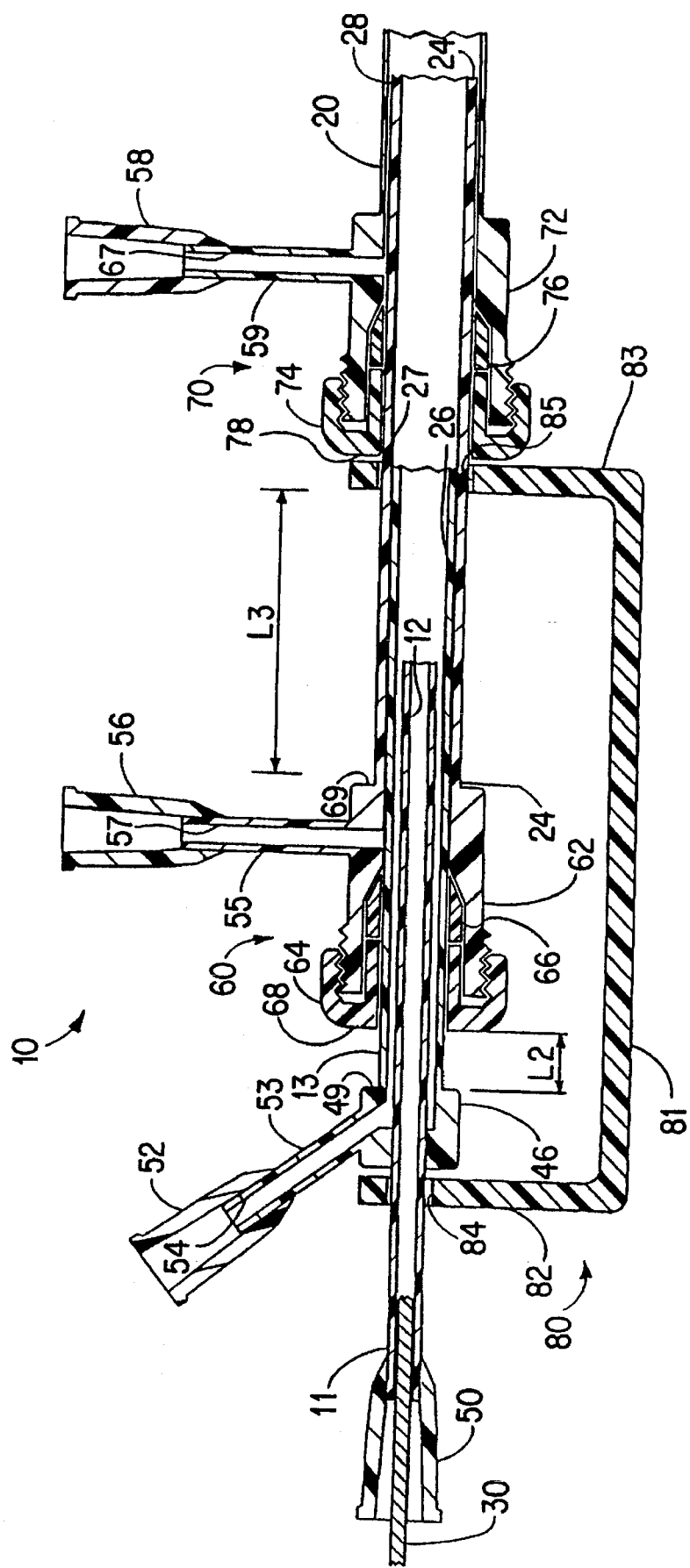
FIG. 3 is longitudinal cross section of a proximal portion of the integrated, dual-function catheter system illustrating means for guide wire and fluid access to various portions of the catheter system.

FIGS. 1, 2 and 3 illustrate an integrated dual-function catheter system consisting of an integrated catheter 10, a guide wire 30 and a stent 40. The integrated catheter 10 includes a slideable outer sheath 20, an outer tube 13, an inner tube 11, a pusher tube 24, an expandable balloon 16, two Tuohy-Borst fittings 60 and 70, four female Luer fittings 50, 52, 56 and 58 and a yoke 80. The catheter 10 is capable of being advanced over the guide wire 30.

FIG. 1 shows that the inner tube 11 has a distal portion 11A that extends for a considerable distance beyond the distal end of the balloon 16. Also the distal portion 11A has a distal end 11B that has a conical taper. Because of the conical shape of the distal end 11B and because the distal portion 11A of the inner tube 11 is highly flexible, the integrated catheter 10 can readily track over a highly flexible guide wire 30. The distal end of the balloon 19 is adhesively joined to the proximal end of the distal portion 11A of the inner tube 11. The proximal end of the balloon 16 is adhesively joined to the distal end of the outer tube 13. The annular passageway 26 that lies between the outer surface of the inner tube 11 and the inner surface of the outer tube 13 is in fluid communication with the interior chamber 19 of the balloon 16. A radiopaque marker band 17 mounted on the inner tube 11 indicates the longitudinal center of the balloon 16. The guide wire 30 passes through the central lumen 12 of the inner tube 11.

The outer sheath 20 has a conically shaped, distal portion 22 that (as seen in FIG. 2) has 4 slits 23 that extend in a longitudinal direction. Although FIG. 2 shows 4 slits, any number of slits from 1 to 16 could be used. The purpose of the slits 23 is to allow the outer sheath to be easily pulled back over the stent 40 and pusher tube 24. Within a distal portion of the outer sheath 20 is a stent 40 that lies within a stent containment cavity 42. The stent containment cavity 42 is bounded by the interior surfaces of the outer sheath 20 including its distal portion 22, the outer surface of the outer tube 13, and the distal surface of the radiopaque marker band 25 that is fixedly joined to the distal end of the pusher tube 24. A radiopaque marker band 21 is also fixedly attached to the outer sheath 20 as shown in FIG. 1. The annular passageway 27 lies between the inner surface of the pusher tube 24 and the outer surface of the outer tube 13. The annular passageway 28 lies between the inner surface of the outer sheath 20 and the outer surface of the pusher tube 24.

FIG. 3 is a longitudinal cross section of a proximal portion of the integrated catheter 10 and also shows the guide wire 30 and the yoke 80. The inner tube 11 has a central lumen 12 that extends through a female Luer fitting 50 located at the proximal end of the inner tube 11. The guide wire 30 is adapted to move slideably through the entire length of the lumen 12 thus making the catheter 10 an "over-the-wire" design. "Over-the-wire" designs have great advantages over "fixed wire" designs or designs such as taught by Pinchuk (U.S. Pat. No. 5,019,090) in which there is no guide wire taught at all because "over-the-wire" designs provide greatly improved trackability when advancing the catheters through tortuous coronary arteries.

FIG. 3 also shows the outer tube 13 having at its proximal end an enlarged diameter section 46 which has a distal end surface 49. The section 46 has a side arm 53 with a lumen 54 and a female Luer fitting 52. The lumen 54 is in fluid communication with the annular passageway 26. A source of pressurized fluid such as a hypodermic syringe when attached to the female Luer fitting 52 can be used to inflate and deflate the balloon 16.

The pusher tube 24 has at its proximal end a Tuohy-Borst fitting 60 which has a distal end surface 69. The Tuohy-Borst fitting 60 has a threaded main body 62, a nut 64 having a proximal end surface 68 and an elastomer gland 66. When the nut 64 is tightened down, the gland 66 makes a fluidic seal between the pusher tube 24 and the outer tuber 13. When the nut 64 is loosened, the pusher tube 24 can move slideably over the outer tube 13. The Tuohy-Borst fitting 60 also has a side arm 55 with female Luer fitting 56 and a central lumen 57; which lumen 57 is in fluid communication with the annular passageway 27 that lies between the pusher tube 24 and the outer tube 13.

The Tuohy-Borst fitting 70 situated at the proximal end of the outer sheath 20 has a main threaded body 72, a nut 74 having a proximal end surface 78 and an elastomer gland 76. When the nut 74 is tightened down, the gland 76 makes a fluidic seal against and frictional attachment to the pusher tube 24. When the nut 74 is loosened, the outer sheath 20 is free to move slideably along the pusher tube 24. The Tuohy-Borst fitting 70 also includes a side arm 59 having a female Luer fitting 58 and a central lumen 67 that is in fluid communication with the annular passageway 28 that lies between the outer sheath 20 and the pusher tube 24.

The material(s) selected for the tubes 11, 13, 20 and 24 can be Teflon or an elastomer such as polyurethane or polyethylene. The Tuohy-Borst fittings are typically fabricated from a harder plastic such as PVC or Nylon or a higher durometer of the same elastomer used for the outer sheath 20 or pusher tube 24. The outer surface of the pusher tube 24 and the inner surface of the outer sheath 20 should be treated to form a hydrophilic lubricious coating to reduce friction when the outer sheath is pulled back to release the stent 40. The stent should be coated with a covalently bonded heparin coating, as is well known in the art of biomedical surfaces, to reduce thrombotic complications after stent placement. The stent could also have a hydrophilic lubricious coating on at least its exterior surface to reduce frictional forces when the outer sheath is pulled back to release the stent. That is, the stent would optimally have a heparin coating that was also hydrophilic and lubricious.

The length of the integrated catheter 10 is typically 20 to 150 cm depending on the vessel into which it is to be placed. The outer sheath 20 and pusher tube 24 are typically considerably shorter than the length of outer tube 13. When the outer sheath 20 and pusher tube 24 are pulled back to their most proximal position, the distal end of the outer sheath should be situated at least 3 cm distal to the proximal end of the balloon 16 and typically 10 cm back. When the distal end of the outer sheath 20 is approximately 10 cm back from the proximal end of the balloon 16, the distal portion of the integrated catheter 10 can be advanced through an extended length of narrow stenosis and through tortuously curved arteries without the encumbrance and added stiffness of the pusher tube 24, outer sheath 20 and stent 40 which could limit the catheter's trackability over a guide wire. Once the balloon 16 is placed within a stenosis, and preferably when the balloon is inflated, the outer sheath 20 and pusher tube 24 can be advanced together until the distal end of the outer sheath 20 is located at the proximal end of the balloon 16. The diameter of the catheter will typically vary from 1.0 to 10.0 mm depending on its use. The radiopaque marker bands 17, 21 and 25 are typically made from a dense metal such as an alloy of tantalum, platinum or gold. The yoke 80 is typically made from a fairly rigid plastic such as PVC.

FIG. 1 defines the length L1 measured from the distal end of the outer sheath 20 to the proximal end of the balloon 16. Although L1 could be 0, this would place the sheath 20, pusher tube 24 and stent 40 sufficiently close to the distal end of the integrated catheter 10 that it could prevent the easy advancement of the system through the tortuous curvature of coronary arteries. If however, L1 was initially set at a length of at least 0.5 cm and preferably 3 to 20 cm, then the additional stiffness caused by the lack of flexibility of the outer sheath 20, pusher tube 24 and stent 40 would not prevent the balloon 16 from being advanced over the guide wire 30 and into an arterial stenosis. Although L1 might be initially set at, let us say, 5 cm, if placing of the distal portion of the integrated catheter 10 into coronary vasculature was made difficult because of the stiffness of the outer sheath 20, outer tube 24 and stent 40, then the Tuohy-Borst fitting 60 (FIG. 3) could be loosened and the length L2 reduced, thus increasing the length L1.

A method for using the "over-the-wire" design, integrated catheter 10 for the treatment of an obstructed coronary artery would be as follows:

1. By conventional means, an introducer sheath and a coronary guiding catheter are inserted at the groin and the guiding catheter's distal end is advanced until it is situated within the ostium of a coronary artery.

2. Saline solution is flushed through each of the three annular passageways 26, 27 and 28 and the central lumen 12 of the catheter 10 by means of the four female Luer fittings 50, 52, 56 and 58.

3. A guide wire 30 that has been pre-loaded into the integrated catheter 10 is advanced with the catheter 10 through the guiding catheter, and the guide wire 30 is then advanced through a coronary artery blockage.

Figure 4A:
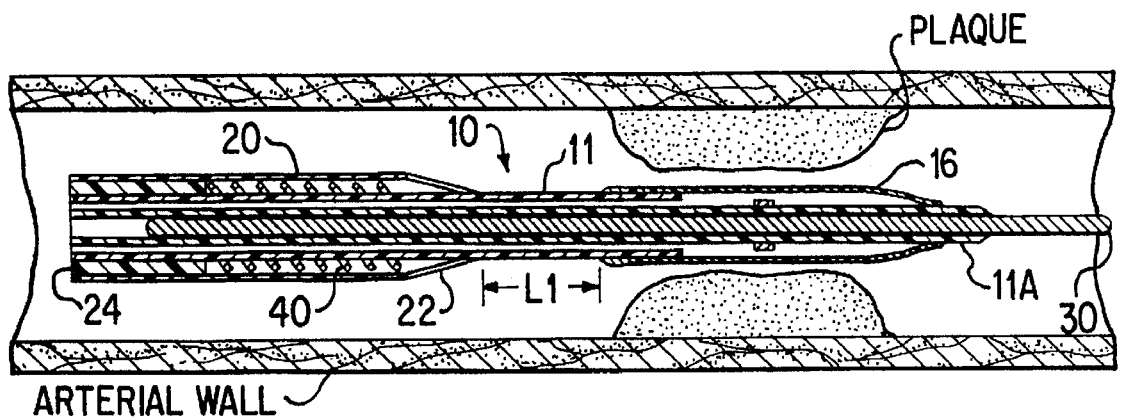
FIG. 4A is a longitudinal cross section of a distal portion of the integrated catheter system showing various portions of the balloon and the stent and showing an unexpanded balloon placed within an arterial stenosis.

4. The catheter 10 is further advanced over the guide wire 30 until the distal end portion 11A of the inner tube 11 lies just distal to the blockage as shown in FIG. 4A. This is accomplished with the pusher tube 24 and the outer sheath 20 in their most proximal positions which occurs with a typical the length L3 (as shown in FIG. 3) that is equal to L1 plus the length of the stent plus the length of the conical distal portion 22 plus approximately 0.5 cm. The length L3 is set so as to prevent the stent from being displaced beyond the distal end of the balloon 16. The nuts 64 and 74 of the Tuohy-Borst fittings 60 and 70 are each initially screwed down tightly to frictionally join the outer sheath 20 to the pusher tube 24 and the pusher tube 24 to the outer tube 13.

Figure 4B:
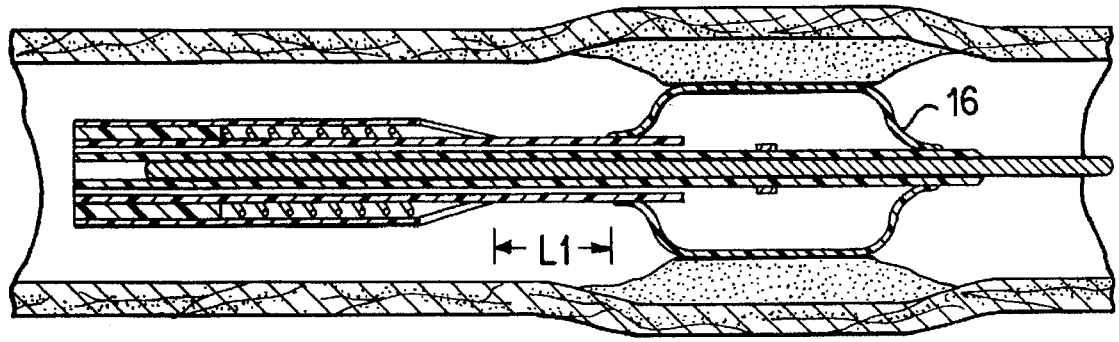
FIG. 4B shows the balloon in its deployed (expanded) state.

5. A fluid pressurization means is then joined to the Luer fitting 52 and the balloon 16 is inflated (as shown in FIG. 4B) to an outside diameter between 2.0 and 5.0 mm depending on the nominal size of the coronary artery in which the blockage occurred.

Figure 4C:
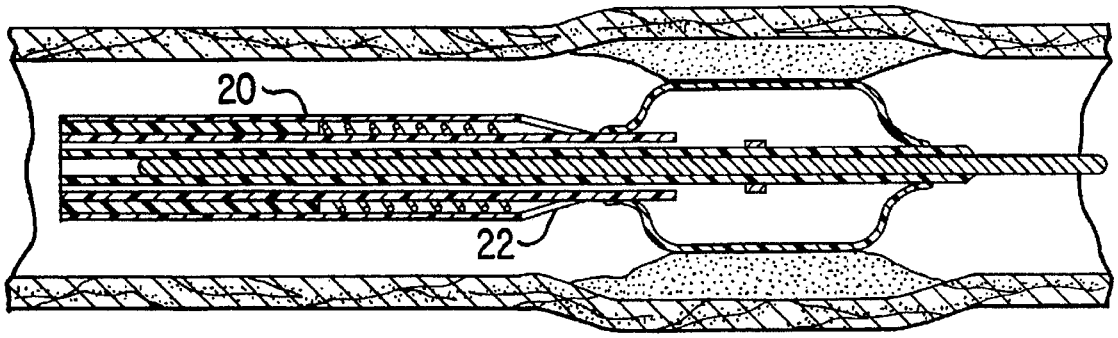
FIG. 4C shows the outer sheath, stent and pusher tube advanced in a distal direction until the distal end of the outer sheath is adjacent to the proximal end of the balloon.

6. While the balloon is inflated, the nut 64 of the Tuohy-Borst fitting 60 is loosened and the pusher tube 24 and outer sheath 20 (which are frictionally joined together by the Tuohy-Borst fitting 70) are advanced forward together in a distal direction thus decreasing the length L3 until the distal end of the conically shaped distal portion 22 of the outer sheath 11 is in contact with the proximal end of the balloon 16; i.e., L1=0. This configuration is shown in FIG. 4C.

Figure 4D:
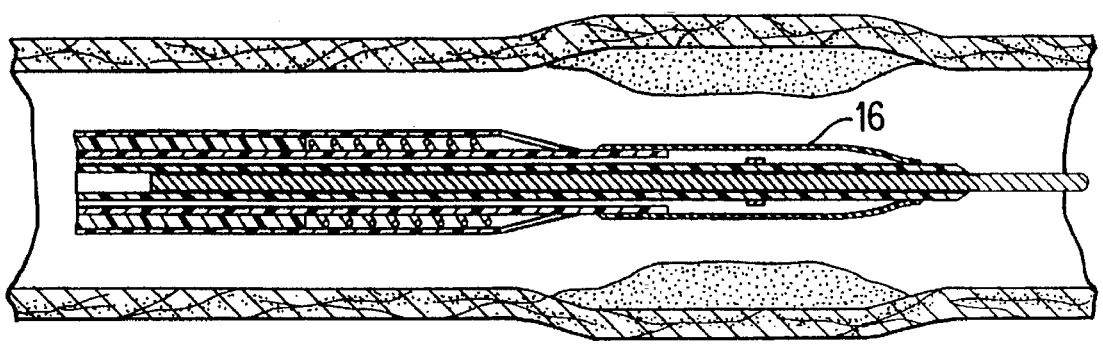
FIG. 4D shows the balloon deflated.

7. The balloon 16 is then deflated as shown in FIG. 4D.

Figure 4E:
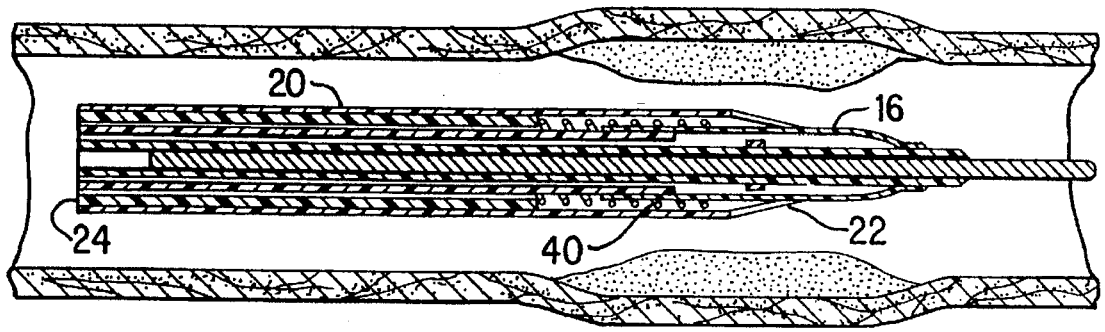
FIG. 4E shows the distal end of the sheath assembly being advanced over the deflated balloon.
Figure 4F:
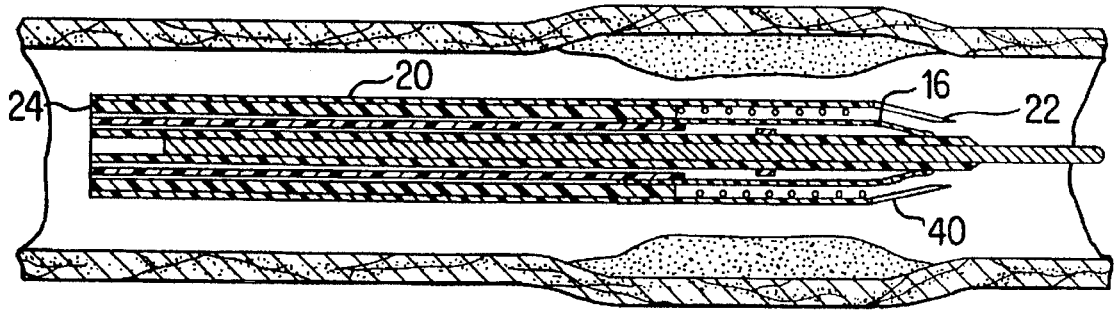
FIG. 4F shows the sheath assembly in its most forward position relative to the balloon.
Figure 4H:
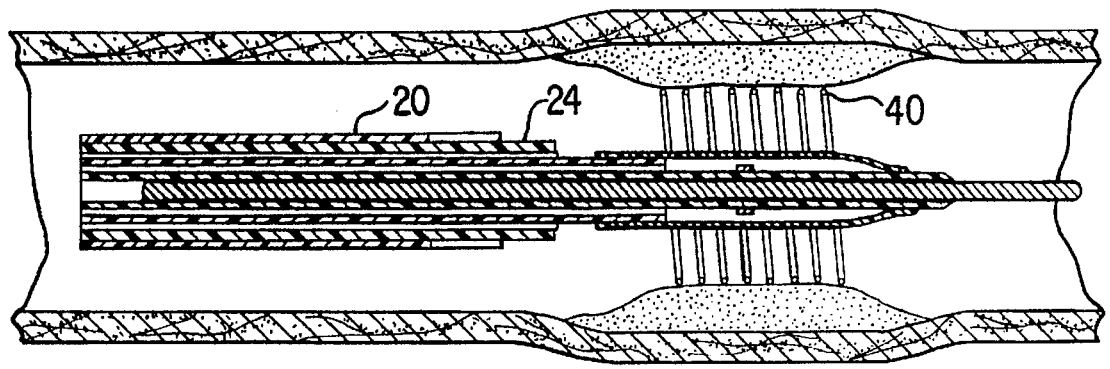
FIG. 4H shows the balloon as it is expanded to place a balloon expandable stent into the arterial wall or to further imbed a self-expanding stent into the arterial wall.
Figure 4H:
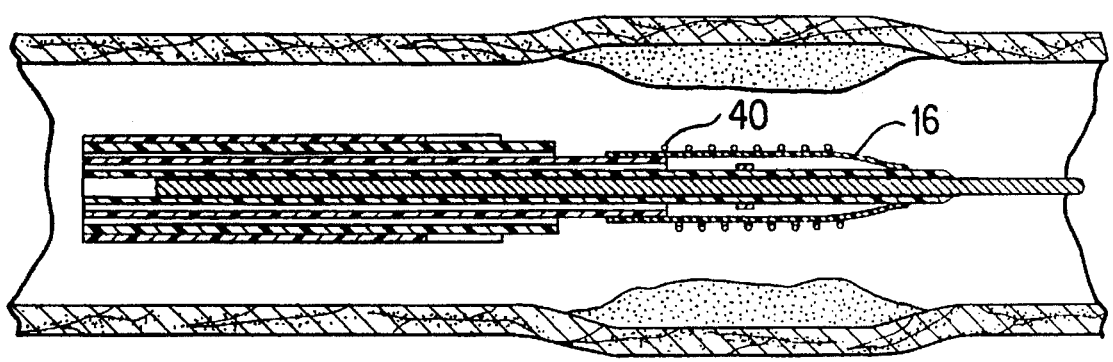
Figure 4H:
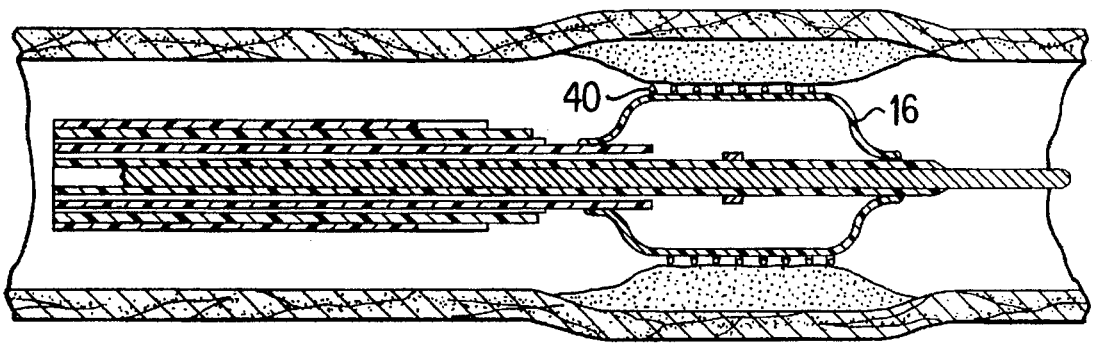
Figure 4I:
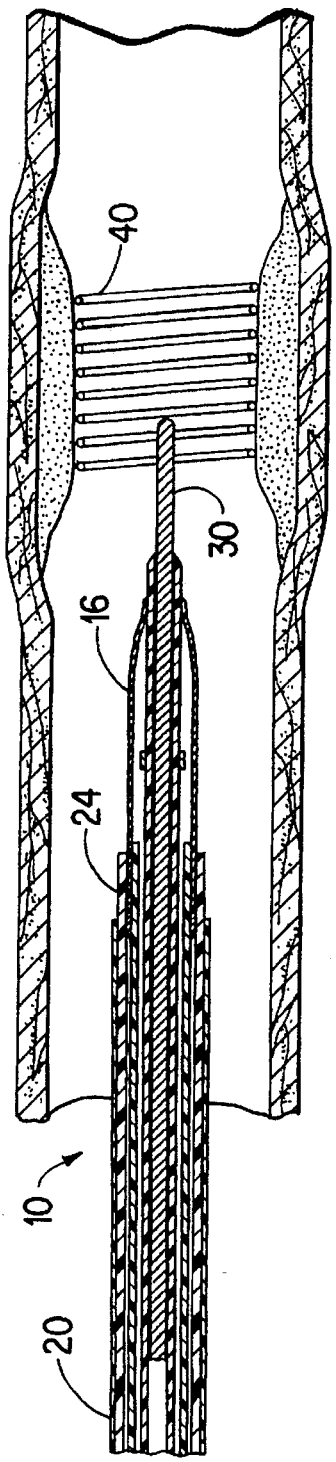
FIG. 4I shows the stent in place with the catheter system being removed from the artery.
Figure 5:
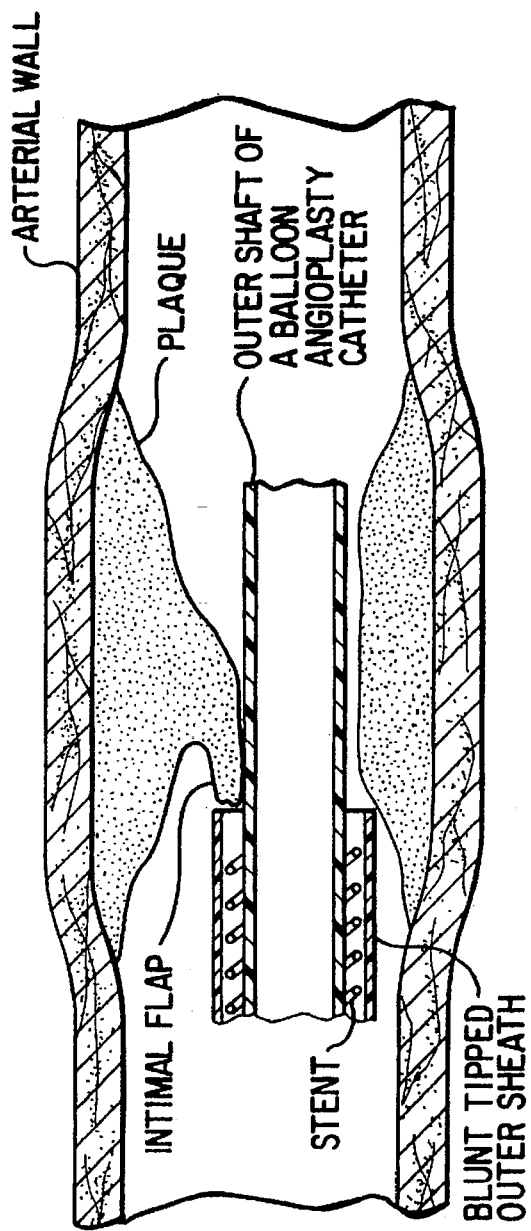
FIG. 5 illustrates how a prior art blunt tipped outer sheath of an integrated stent and balloon angioplasty catheter can be made dysfunctional because of an intimal flap formed in the plaque after balloon dilatation.

8. The pusher tube 24 and outer sheath 20 are then advanced together over the deflated balloon as shown in FIG. 4E further reducing the length L3. It is important to note that any intimal dissection resulting in an intimal flap will be lifted away from the surface of the deflated balloon 16 by the pointed distal end of the conical distal end portion 22 of the outer sheath 20 which conical distal end is in fact a frustrum of a cone whose distal end intersects the outer shaft of the balloon angioplasty catheter at an acute angle as clearly shown in FIGS. 1 and 4A to 4I inclusive. This is in contradistinction to all prior art integrated catheter devices which have outer sheaths whose ends are blunt and therefore could have their forward motion stopped by an intimal flap that was in contact with the outer surface of either the balloon or the outer shaft of a balloon angioplasty catheter. This disadvantage of the prior art that can prevent proper functioning of an integrated catheter is shown in FIG. 5.

9. FIG. 4F shows that the outer sheath 20 and pusher tube 24 have been advanced until the stent 40 lies over the deflated balloon 16. The yoke 80 is dimensioned to prevent the pusher tube 24 from being extended beyond the point shown in FIG. 4F thus eliminating the possibility that the stent would be deployed at a point beyond the distal end 11B of the inner tube 11.

10. FIG. $4G_1$ illustrates that a self-expanding, shape memory metal (such as Nitinol) stent would expand radially outward to engage the interior surface of the dilated stenosis when the outer sheath 20 is pulled back. Before the outer sheath 20 is pulled back, the nut 64 of the Tuohy-Borst fitting 60 is tightened down to frictionally join the pusher tube 24 to the outer tube 13, and the nut 74 is loosened so that the outer sheath 20 can be pulled backward in a proximal direction until the stent 40 is released.

11. FIG. $4G_2$ illustrates that a balloon expandable stent (as opposed to a self-expanding stent) would remain in contact with the outer surface of the deflated balloon 16 after the outer sheath 20 is pulled back. A slight inflation of the balloon 16 before the sheath 20 is pulled back may be necessary to hold the stent 40 during the pulling back of the sheath 20.

12. FIG. 4H shows how either the self-expanding or balloon expandable stent would look after the balloon 16 is expanded radially outward. In the case of the self-expanding stent, the purpose of the balloon expansion is to push back the plaque to allow a comparatively fragile, shape memory metal stent to reach its final, fully expanded shape. Until that final shape is achieved, shape memory metal stents do not exert a sufficiently strong outward radial force to outwardly deform hard plaque. However, once the fully expanded shape of the stent is achieved with the assistance of the balloon 16, shape memory metal stents are sufficiently strong to maintain a considerable outward force on the dilated plaque. At no time does the expanded balloon deform a shape memory metal by exceeding the elastic limit of the metal of the stent. On the other hand, the balloon expandable stent shown in FIG. $4G_2$ is severely deformed by the expanding balloon 16, thus exceeding the elastic limit of the metal of the stent. This creates a plastic deformation of the stent so that it will retain its expanded shape as shown in FIG. 4I.

13. The balloon 16 is then deflated (as shown in FIG. 4I) and the catheter 10 and the guide wire 30 are removed from the artery.

14. The guiding catheter and introducer sheath are then removed using appropriate methods that are well known in interventional cardiology.

As described in steps 1 through 14 above, a single integrated catheter 10 can be used for initial dilatation of a blockage in a vessel, for release of a stent within that vessel at the site where the dilatation occurred, and the balloon can be then reinflated to allow a shape memory metal stent or a balloon expandable stent to expand to a final, fully expanded state. Thus the requirement for one or more separate balloon dilatation catheters and a separate stent delivery catheter has been eliminated with a resulting cost economy and a decrease in the time required to perform this procedure.

Figure 6A:
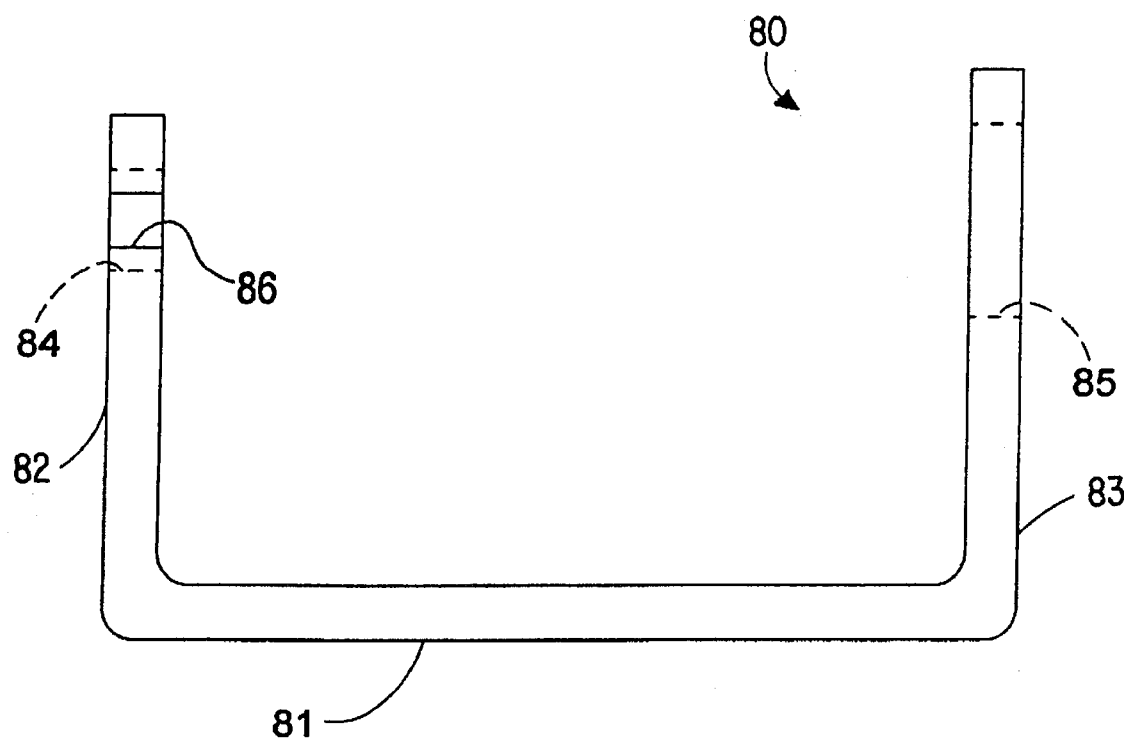
FIG. 6A is a side view of a yoke used to prevent excessive longitudinal displacement of the pusher tube.
Figure 6B:
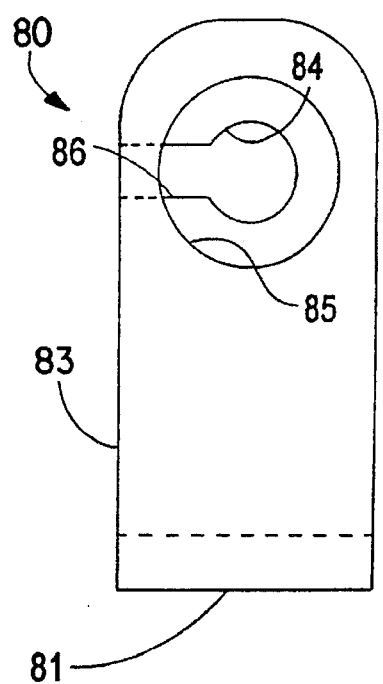
FIG. 6B is an end view of the yoke.

It would be highly disadvantageous if it were possible for the invention described herein to advance the stent 40 beyond the distal end of the inner tube 11. If that occurred, the stent could be set free at an incorrect location within the artery. To disallow that possibility, a displacement limiting means located outside the patient's body must be utilized. One such displacement limiting means is the yoke 80 that is shown in FIGS. 3, 6A and 6B. The yoke 80 has a main longitudinal section 81, a proximal end piece 82 having a hole 84 and a slit 86 and a distal end piece 83 having a hole 85. The yoke 80 is assembled onto the integrated catheter 10 by first sliding the hole 85 over the pusher tube 24 before the Tuohy-Borst fitting 70 and outer sheath 20 are slid over the pusher tube 24. Then the slit 86 is pushed over the proximal end of the inner tube 11 as is shown in FIG. 3. A pusher tube longitudinal displacement limiting means assures that the stent 40 will not be positioned to a more distal position relative to the balloon 16 than that position shown in FIG. 4F.

Figure 7A:
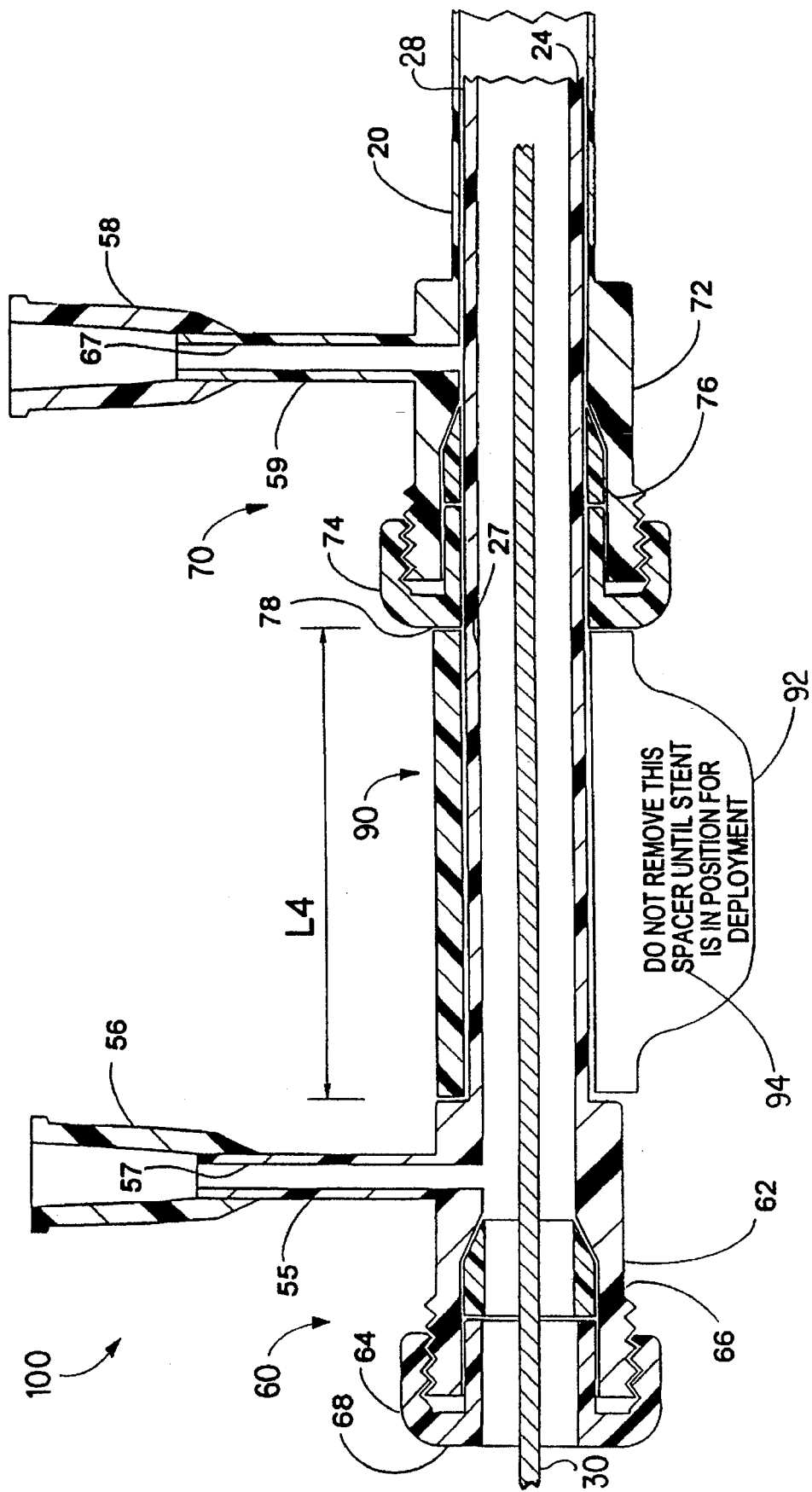
FIG. 7A is a longitudinal cross section of an alternative embodiment of a sheath assembly (including a removable spacer) as placed over a guide wire.

FIG. 7A illustrates a sheath assembly 100 that consists of the outer sheath 20, pusher tuber 24, Tuohy-Borst fitting 60, Tuohy-Borst fitting 70 and spacer 90 which assembly 100 can be advanced over the guide wire 30 without using a balloon angioplasty catheter. Thus the sheath assembly 100 could be used as a separate means for inserting a stent if prior balloon dilation was not required or to act as a guide for the introduction or exchange of balloon dilation catheters. A unique feature shown in FIG. 7A is a removable spacer 90 that is used to prevent inadvertent release of the stent by disallowing the pusher tube 24 from being advanced in a forward direction relative to the outer sheath 20 until the spacer 90 is removed. FIGS. 7A, 7B, 8A and 8B show the spacer 90 having a pull tab 92, warning label 94, cylindrical portion 96 and slit 98. The slit 98 allows the elastomer material of the spacer 90 to be deformed so that it can be placed onto or pulled off from the pusher tube 24. The length L4 of the spacer 90 is typically equal to the length of the stent 40, plus the length of the conical distal portion 22 of the outer sheath 20 plus approximately 0.5 cm. The length L4 is set so that when the spacer 90 is removed, the outer sheath 20 can be pulled back relative to the pusher tube so that the stent 40 can be released.

Figure 7B:
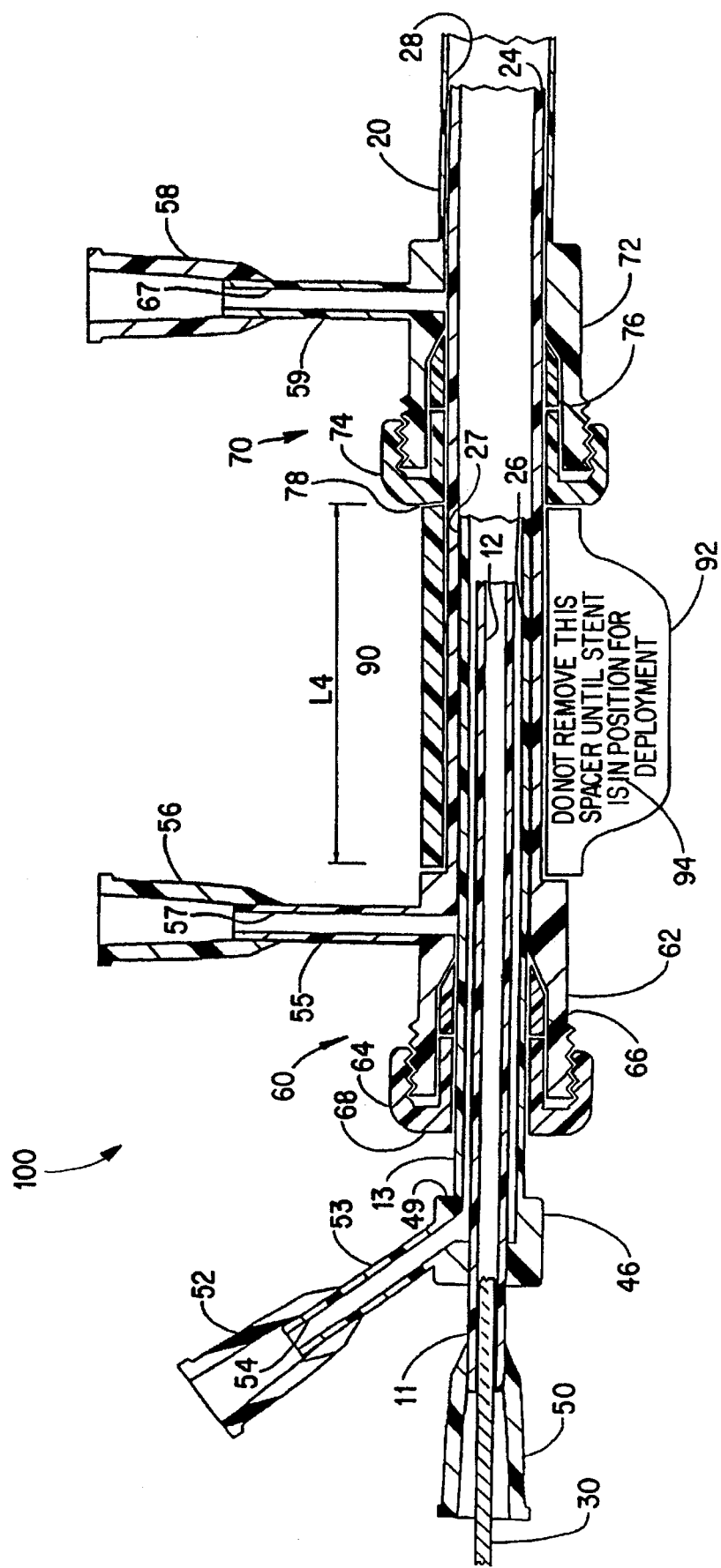
FIG. 7B is a longitudinal cross section of an alternative embodiment of the sheath assembly placed over a balloon angioplasty catheter and a guide wire.
Figure 8A:
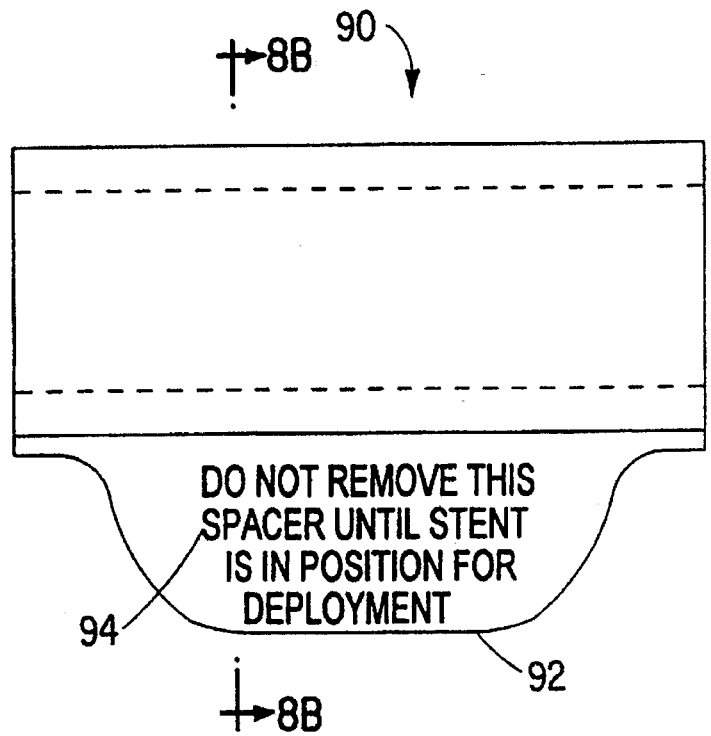
FIG. 8A is a side view of a removable spacer used to prevent inadvertent release of the stent.
Figure 8B:
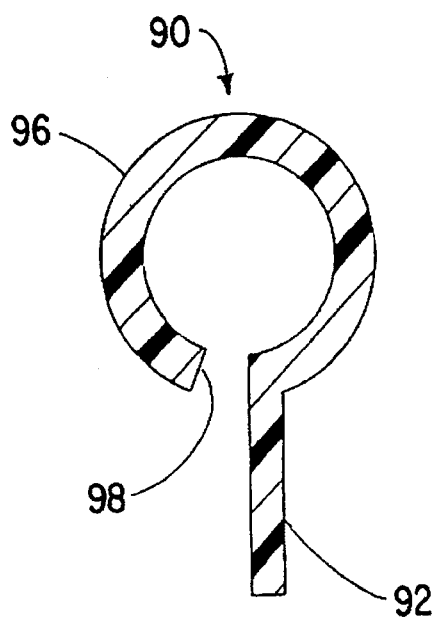
FIG. 8B is a cross section at section 8B—8B of FIG. 8A showing a transverse cross section of the spacer.

FIG. 7B illustrates how the sheath assembly 100 can be placed over a typical balloon angioplasty catheter (as previously shown in FIGS. 1, 2, 3 and 4A to 4I). The only difference being that the spacer 90 is used and not the yoke 80. It is also possible to utilize a combination of yoke 80 and spacer 90 or other equivalent means to prevent the inadvertent release of the stent.

It should also be understood that the invention described herein can be used with a variety of angioplasty balloon catheters including those with fixed guide wires at their distal end; i.e., "fixed wire" catheters. In fact, the sheath assembly 100 shown in FIG. 7A could be used with a large variety of balloon angioplasty catheters as selected by the physician at the time of the vessel opening procedure.

It should be further understood that one, two or more radiopaque marker bands could be used with any integrated design.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. An integrated catheter system for performing a dilatation procedure within a vessel of a human body and for placement of a stent within that region of the vessel that underwent dilatation, the catheter system comprising:

a balloon angioplasty catheter having a distal end and a balloon located near the catheter's distal end, the balloon having a proximal end fixedly attached to an elongated outer tube and a distal end attached to an elongated inner tube, the balloon being able to be inflated to an inflated state and deflated to a deflated state;

a first elongated cylindrical tube which is a pusher tube having a proximal end and a distal end and being adapted to move slideably over the balloon angioplasty catheter;

a second elongated cylindrical tube which is an outer sheath, the pusher tube being adapted to move slideably within the outer sheath which has a stent containment cavity containing a radially expandable stent situated near the sheath's distal end, the stent containment cavity being bounded at its distal end by a distal portion of the outer sheath in the shape of a frustrum of a cone having a distal end that intersects the outer tube of the balloon angioplasty catheter at an acute angle, the stent containment cavity being bounded at its proximal end by the distal end of the pusher tube, said combined slideable pusher tube, said radially expandable stent and said outer sheath being slideably displace able in a distal direction over said balloon while maintaining said outer sheath distal end frustrum cone shape, the outer sheath and the pusher tube each having separate proximal pullback means adapted to lie outside the human body for pulling the sheath back relative to the pusher tube so as to release the radially expandable stent from the stent containment cavity so that the stent can be expanded radially outward against the vessel wall.

2. The catheter system of claim 1 wherein the balloon angioplasty catheter is of the "over-the-wire" design having a central lumen extending throughout the entire length of the balloon angioplasty catheter.

3. The catheter system of claim 2 further comprising a flexible guide wire adapted to be advanced through the central lumen of the balloon angioplasty catheter.

4. The catheter system of claim 1 wherein the distal end of the frustrum of a cone is adapted to be moved with a snug fit over the balloon when the balloon is in its deflated state.

5. The catheter system of claim 4 wherein the conically shaped distal portion includes at least one longitudinally placed slit to allow the outer sheath to be easily pulled back over the stent and over the pusher tube.

6. The catheter system of claim 1 wherein the pusher tube includes a radiopaque marker band at its distal end.

7. The catheter system of claim 1 wherein the radially expandable stent is a balloon expandable stent.

8. The catheter system of claim 1 wherein the radially expandable stent is a self-expanding stent.

9. The catheter system of claim 8 wherein the radially expandable stent is formed of a shape memory alloy, shape memory alloy being Nitinol.

10. The catheter system of claim 1 wherein the proximal pullback means is a Tuohy-Borst fitting.

11. The catheter system of claim 1 wherein the integrated catheter has four separate lumens, each lumen being accessible for flushing from the catheter's proximal end.

12. The catheter system of claim 11 wherein three of the lumens are annular passageways and the central lumen is generally of a cylindrical geometry.

13. The catheter system of claim 1 wherein at least one radiopaque marker band is used to indicate the location of the stent containment cavity.

14. The catheter system of claim 1 further comprising a longitudinal displacement limiting means to prevent the inadvertent release of the stent beyond the distal end of the inflatable balloon.

15. The catheter system of claim 1 further comprising a longitudinal displacement limiting means to prevent the inadvertent release of the stent by disallowing inadvertent pullback of the outer sheath relative to the pusher tube.

16. The catheter system of claim 15 wherein the longitudinal displacement limiting means is a removable spacer.

17. A method for performing balloon angioplasty followed by placement of a self-expanding stent within a vessel of a human body, the method comprising the following steps:

(a) inserting an integrated catheter system including a catheter having a distal end, said catheter system including an inflatable balloon and a self expanding stent within a stent containment cavity all located near the catheter's distal end into the vessel of a human body;

(b) performing balloon angioplasty dilatation at a site in the vessel;

(c) deflating the balloon and advancing the stent until it is situated over the deflated balloon, the balloon retaining its position generally within the dilatation site; and (d) pulling back an outer sheath thus allowing the self-expanding stent to deploy at the dilatation site.

18. The method of claim 17 further comprising the step of reinflating the balloon so as to assist the stent in obtaining its fully deployed state.

19. A method for performing balloon angioplasty followed by stent placement within a coronary artery of a human body, the method comprising the following steps:

(a) inserting into the vessel of the human body an integrated catheter system consisting of a balloon angioplasty catheter coaxially placed within a stent delivery catheter, the stent delivery catheter having distal and proximal ends, the balloon angioplasty catheter having a distal section wherein an inflatable balloon is located, the balloon having distal and proximal ends;

(b) placing the stent delivery catheter's distal end more than 0.5 cm back in a proximal direction from the proximal end of the balloon as the integrated catheter system is advanced through the coronary vascular so that the stiffness of the stent does not interfere with tracking of the distal section of the balloon angioplasty catheter over a flexible guide wire;

(c) advancing the integrated catheter system until the balloon angioplasty catheter is placed within a coronary artery stenosis;

(d) performing balloon angioplasty dilatation of the stenosis;

(e) deflating the balloon;

(f) advancing the stent over the deflated balloon; and (g) pulling back an outer sheath thus allowing the stent to be deployed at the dilatation site.

* * * * *